United States Patent [19]

Spangler

[11] 4,399,816
[45] Aug. 23, 1983

[54] WOUND PROTECTOR WITH TRANSPARENT COVER

[76] Inventor: George M. Spangler, 15704 Campbell, Harvey, Ill. 60426

[21] Appl. No.: 343,538

[22] Filed: Jan. 28, 1982

Related U.S. Application Data

[63] Continuation-in-part of Ser. No. 131,153, Mar. 17, 1980, abandoned.

[51] Int. Cl.$^3$ .............................................. A61F 13/00
[52] U.S. Cl. .................................................... 128/154
[58] Field of Search ............... 128/132 R, 132 D, 133, 128/154, 155

[56] References Cited

U.S. PATENT DOCUMENTS

| | | | |
|---|---|---|---|
| 679,918 | 8/1901 | Shears | 128/154 |
| 697,637 | 4/1902 | Lee | 128/154 |
| 720,812 | 2/1903 | Johnson | 128/154 |
| 2,221,758 | 11/1940 | Elmquist | 128/132 R |
| 2,367,690 | 1/1945 | Purdy | 128/132 R |
| 2,443,140 | 6/1948 | Larsen | 128/154 |
| 2,663,020 | 12/1953 | Cushman | 128/132 R |
| 3,026,874 | 3/1962 | Stevens | 128/154 |

FOREIGN PATENT DOCUMENTS

| | | | |
|---|---|---|---|
| 1914096 | 10/1970 | Fed. Rep. of Germany | 128/154 |
| 701472 | 3/1931 | France | 128/154 |
| 12042 | 2/1896 | Switzerland | 128/154 |
| 288220 | 7/1927 | United Kingdom | 128/154 |

*Primary Examiner*—John D. Yasko

[57] ABSTRACT

The wound protector comprises a base pad of a pliable fibrous or foamed non-allergenic material in an angular form which may be circular, rectangular, square, oval or triangular. Since the purpose of the wound protector is to prevent the wounded portion of the body from being contacted by anythingother than medicants, the central opening of the base pad must be larger than the wounded area about which it is to be placed. A marginal ledge is formed in the top surface of the base pad around the inner opening for the purpose of receiving surgical gauze or sponge containing a medicant, should such be required, for treatment of the wounded area. As the wound protector is to be provided with a transparent cover, the top surface of the base pad between the marginal ledge and the outer vertical surfaces of the pad must be of sufficient width to support the transparent cover as well as provide adequate area for securing at least a part of the cover to the pad. The transparent cover is of a transparent plastic material having some flexibility but lying flat on the upper surface of the base pad when in the normal position. The transparent cover is of the same shape as the base pad and is secured at one side by a permanent adhesive material. While the transparent cover will normally lie flush with the upper surface of the base pad after it is adhered to the pad, a tacky adhesive may be employed on the side of the top surface of the pad opposite the side securing the cover thereto to permit the cover to be lifted up for treatment purposes and then held firmly but releasably to the pad after the treatment. The wound protector is applied to the body area by a non-allergenic adhesive material.

6 Claims, 7 Drawing Figures

WOUND PROTECTOR WITH TRANSPARENT COVER

This application is a continuation-in-part of my application Ser. No. 131.153 filed Mar. 17, 1980, now abandoned.

FIELD OF THE INVENTION

The present invention lies in the area of bandages for wounds and sores and more particularly in the area of bandages which provide protection against the wound being touched or contaminated and which provides for visual observation of the condition of the wound without removing the bandage.

BACKGROUND OF THE INVENTION

Wounds or sores on any surface of the body are generally treated by applying an appropriate medicant to the injured area and then generally it is the practice to cover the wounded area with sterile surgical gauze or "sponge" and then utilize bandaging to hold the surgical gauze in position over the wound, thus forming a bandage. Such a bandage forms a covering which protects the wound area from additional injury or contamination which might worsen the condition. However, such bandages do not readily reveal the condition of the treated wound or sore. With this type of bandaging, the condition of the treated wound can be determined only by removing the bandage. Often the surgical gauze has adhered to the wounded area and the removal of the gauze for examination and treatment is frequently very painful. Additionally, the contact of the surgical gauze with the wounded area frequently absorbs the medicant thus preventing maximum utilization of the medicant on the wound. If the surgical gauze does adhere to a wounded area, its removal aggravates the condition of the wound and thus retards the healing.

Prior disclosures which have addressed this problem are U.S. Pat. Nos. 2,443,140; 2,367,690; 2,221,758; 697,637; 720,812; German Offenlegungsschrift No. 1,914,096; and German Pat. No. 120,402; and British Pat. No. 288,220.

The wound protectors in the foregoing disclosures generally provide for protection of the wounded area and visibility of the wound itself. Generally speaking, the wound protectors in the foregoing disclosures have rigid portions to protect the wound area. U.S. Pat. Nos. 2,221,758 and 720,812 employ resiliant felt-like pads, but have the transparent covers firmly secured to the upper surface of the pad.

SUMMARY OF THE PRESENT INVENTION

The present invention comprises a base pad having a central opening with vertical walls. The central opening may be oval, circular, rectangular, or square, and the exterior wall of the base pad may be vertical or at least a portion of it tapered inwardly to minimize the effect of clothing rubbing against the pad. The pad is of sufficient thickness to not only provide protection to the wound area, but also to provide for a ledge in the upper surface extending outwardly from the inner or central opening. This ledge may be optionally utilized to hold surgical gauze or similar hygienic material which may contain medicants for continual dosage of a wound area or may be employed to absorb some of the liquid. The bottom surface of the base pad is covered with an adhesive material which is non-allergenic and, while providing good bonding of the base pad to the skin, will permit direct removal of the base pad without further damage to the skin. The central opening of the base pad is provided with a generally transparent cover which is securely adhered to one side of the central opening on the upper surface of the pad, preferably the longitudinal axis. The cover should have some flexibility to permit the free end being lifted upward and yet sufficient rigidity to generally remain in the flat or planar state on the upper surface of the base pad. Selectively the free end of the cover may have its underside covered with a "tacky" adhesive which will hold it against the upper surface of the base pad in that area and yet will permit the cover to be raised.

BRIEF DESCRIPTION OF THE DRAWINGS

The invention may be seen in the accompanying drawings in which the embodiment shown therein is illustrative only and is not limiting as to the configuration of the various components as shown therein.

DETAILED DESCRIPTION OF THE INVENTION

Figure 1:
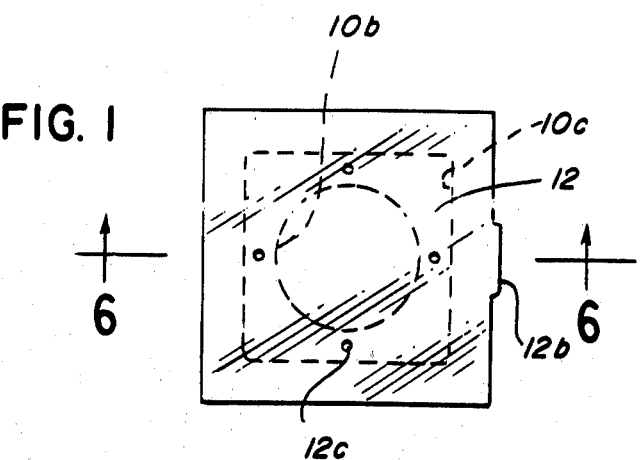
FIG. 1 is a plan view of the present invention.

Referring now to the drawings, it will be seen that the present invention comprises two basic components, a base pad 10 and a cover 12.

Figure 7:
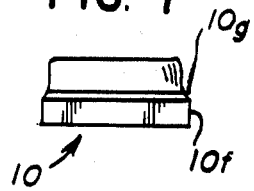
FIG. 7 is a partial plan view of the base pad of the present invention showing a variation in the outer wall.
Figure 2:
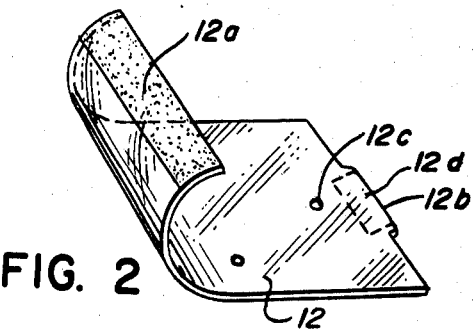
FIG. 2 is a perspective view of the cover of the present invention rolled at one side to expose an adhesive area.
Figure 3:
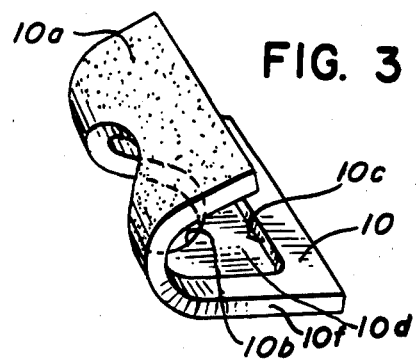
FIG. 3 is a similar view of the base pad of the present invention to expose part of an entire adhesive area.
Figure 4:
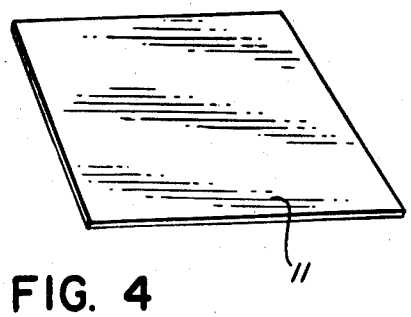
FIG. 4 is a perspective view of a protective film applied to the bottom of the base pad of the present invention.
Figure 5:
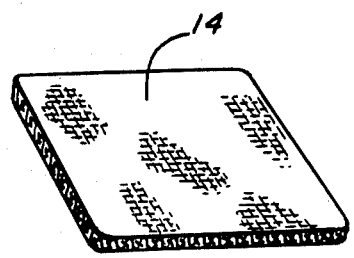
FIG. 5 is a perspective view of a surgical gauze or sponge which may be employed with the present invention.

The base pad 10 may be rectalinear as shown or may be oval, circular, octagonal, or any other shape as the wound area and the location of the wound may require. The base pad 10 is made of a felt-like material or a closed-cell resilient thermoplastic material, one primary consideration being that the base pad material be non-allergenic. The base pad material must be sufficiently flexible so that if necessary the undersurface of the base pad can conform to the shape of the body member upon which it is placed. The base pad must be of sufficient thickness to insure that when the wound protector is placed about the wound area, no part of the wound protector, including the surgical gauze or sponge to be described later will contact the wound area. Normally, the base pad would have a thickness of about an eighth of an inch, but large sizes of the wound protector covering larger portions of the body may require a pad of increased thickness. The undersurface of the base pad is covered with a non-allergenic adhesive 10a for adherence of the base pad to the skin surrounding the wound area. Until such time as the wound protector is used, the adhesive area 10a is protected by a releasable film 11 which not only protects the adhesive area, but also prevents contamination of the interior of the wound protector prior to its use. The base pad 10 has a central opening 10b of a size greater than the wound area over which the wound protector is to be in place. The central opening may be circular as shown or it may have the outer surface configuration of the base pad. The wall of the central opening is preferably perpendicular as would be the outer wall 10f of the base pad 10. In those instances where the wound protector may be in rubbing contact with clothing or any other article which would tend to push against the outer vertical wall of the wound protector, the outer vertical wall may be at least partially chamfered as seen in FIG. 7 at 10g. The upper surface of the base pad 10 also contains a recess 10c surrounding the central opening 10b thereby forming a ledge 10d.

Figure 6:
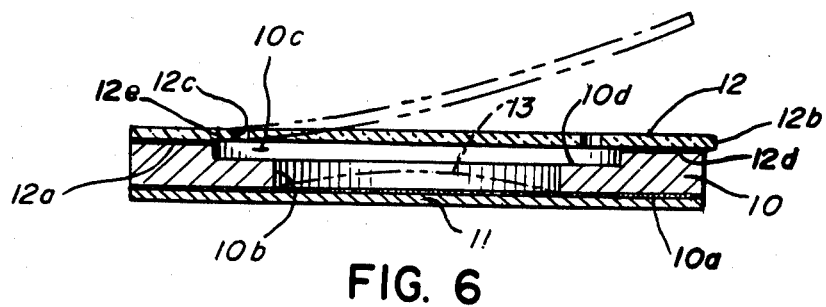
FIG. 6 is a sectional view of the present invention along the plane 66 in FIG. 1.

The cover 12 of the wound protector is of a transparent, semi-rigid plastic material. The material for the cover must have sufficient rigidity to lie flat on the upper surface of the base pad and get sufficient flexibility so that one end of the cover can be raised. That portion of the cover opposite the end which is to be raised contains an adhesive 12a which securely fastens that portion of the cover 12 to the upper surface of the base pad as shown in FIG. 6. To facilitate lifting the cover 12 at the other end, there is provided an outwardly extending lip 12b. Since the cover 12 may be accidentally or inadvertently lifted as during sleep, the undersurface of that portion of the cover containing the lip is coated on the underside with a tacky adhesive 12b which will hold the cover in place and yet will permit the cover to be lifted without destroying the upper surface of the base pad 10. To facilitate the hinge-like action of the cover 12 at the area where the cover is secured by adhesive 12a to the base pad 10, a fine scoring of the top or undersurface of the cover or both, as shown in 12e may be accomplished prior to assembly. Controlled ventilation is generally beneficial for the healing of both wounds and therefore at least two fine perforations 12c are made through cover 12, the perforations being made in those portions of the cover over the ledge 10d.

In some instances the wound area 13 may require the application or constant contact with a medicant or it may be desirable also to provide a means for absorbing any excess secretion from the wound area. For this purpose there is provided a surgical gauze or sponge 14 which is sterile and is placed on the ledge 10d, the medicant required coating the underside of the sponge 14. The sponge 14 is made of material commonly used for surgical sponges and no particular material is a part of the invention.

To use the wound protector of the present invention, the wound area is treated as necessary, the raisable film 11 is peeled from the underside of base pad 10 which is placed about the wound area and pressed into contact with the surrounding skin. If necessary, the lip 12b is lifted from the top surface of the base pad 10, and the surgical sponge 14 inserted on ledge 10d and the cover 12 then closed, the tacky adhesion 12b holding the cover 12 sufficiently tightly to the upper surface of the base pad.

As shown and described, the present invention provides a wound protector having a low vertical profile with readyease of observation of the wound area and permits treatment of the wound area without removal of the wound protector until such time as the wound area has healed sufficiently. Variations in sizes, shapes and materials will occur to those of ordinary skill in the art, and they are encompassed within the scope of the following claims.

What is claimed is:

1. A wound protector comprising: a planar base pad having a central opening therethrough of an area larger than the wound area to be protected, a recess in the top surface of said base pad forming a ledge around said central opening, said ledge to receive a surgical sponge, said pad being of a non-allergenic material selected from the group consisting of felt-like, nonwoven and closed-cell foamed substances, said pad having a thickness such that a surgical sponge placed in said recess will not contact said wound area, said pad further having a non-allergenic adhesive on its undersurface for adhering said protector to the skin, and a pre-use, releasable foil covering the entire undersurface of said base pad including said central opening to protect said adhesive prior to use of the device; and a flat, transparent cover of the same configuration as said base pad, one side of said cover being secured to the upper surface of said base pad over the length of that side of the base pad and out to the edge of said recess, the opposite side of said cover having an outwardly projecting lip, said cover being semi-rigid and having sufficient flexibility so that when the lip is raised from the base pad, the cover will have a hinge-like action at the area of adhesive securement to the base pad, the undersurface of said cover in said lip area being coated with a second adhesive of a tacky type which will hold the other end of said cover on said base pad and will permit the said other end of said cover to be released from said base portion, said cover further having at least two ventilating openings through said cover, said openings being so positioned on said cover over said ledge.

2. The wound protector according to claim 1, wherein said recess has the same configuration as the exterior of the base pad.

3. The wound protector according to claim 1, wherein said central opening is circular.

4. The wound protector according to claim 1, wherein said central opening has the same configuration as the exterior of said base pad.

5. The wound protector according to claim 1, wherein the exterior configuration of said base pad is selected from the group consisting of rectolinear, circular, oval, multisided, and triangular.

6. The wound protector according to claim 5, wherein at least a portion of the vertical outer surface of said base pad is chamfered.

* * * * *